United States Patent
Mahar

(10) Patent No.: US 9,402,662 B2
(45) Date of Patent: Aug. 2, 2016

(54) SPINAL INSTRUMENTS WITH SET SCREW LOADING AND RETENTION APPARATUS AND METHODS OF USE

(75) Inventor: Andrew Todd Mahar, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 1042 days.

(21) Appl. No.: 13/293,553

(22) Filed: Nov. 10, 2011

(65) Prior Publication Data

US 2012/0123487 A1    May 17, 2012

Related U.S. Application Data

(60) Provisional application No. 61/414,498, filed on Nov. 17, 2010.

(51) Int. Cl.
  *A61F 2/46*    (2006.01)
  *A61B 17/70*    (2006.01)

(52) U.S. Cl.
  CPC .................................. *A61B 17/7091* (2013.01)

(58) Field of Classification Search
  CPC ........ A61B 17/56; A61B 17/88; A61B 17/90; A61F 2/30
  USPC ................................................ 606/86 R, 86 A
  See application file for complete search history.

(56) References Cited

U.S. PATENT DOCUMENTS 7,621,918 B2 * 11/2009 Jackson ...................... 606/86 A
2011/0184469 A1 * 7/2011 Ballard et al. ................ 606/279

* cited by examiner

*Primary Examiner* — David Isabella
*Assistant Examiner* — Christine Nelson
(74) *Attorney, Agent, or Firm* — John Chau

(57) ABSTRACT

A spinal instrument with a set screw loading and retention mechanism includes a first tube, a screw slot, and a retention mechanism. The first tube includes an inner lumen disposed concentric and proximate to a head portion of a bone screw. The screw slot is disposed along a portion of the first tube at a distance from the head portion of the bone screw and is configured for loading of a set screw for locking a spinal rod within the head portion of the bone screw. The retention mechanism is disposed along at least a portion of the inner tube configured to selectively retain the set screw. In other features, the first tube includes either an internal rod reduction tube or a screw extender tube.

6 Claims, 13 Drawing Sheets

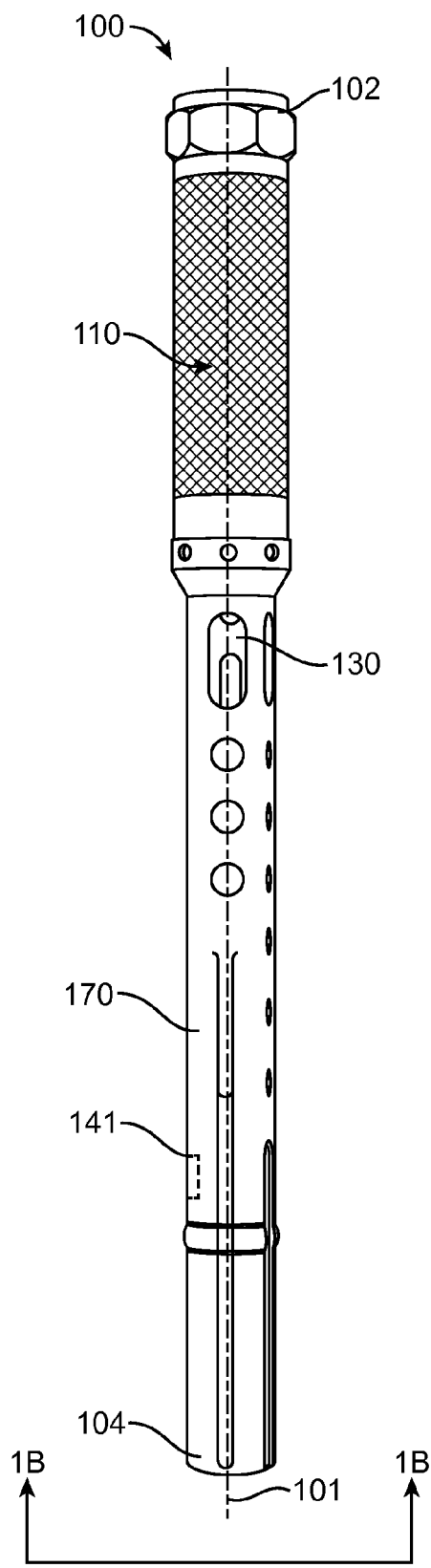
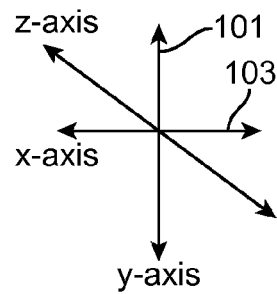
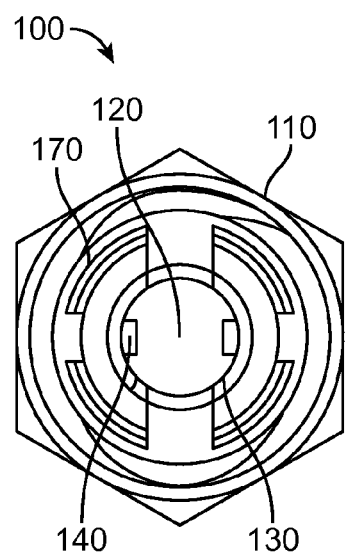
FIG. 1A
FIG. 1B

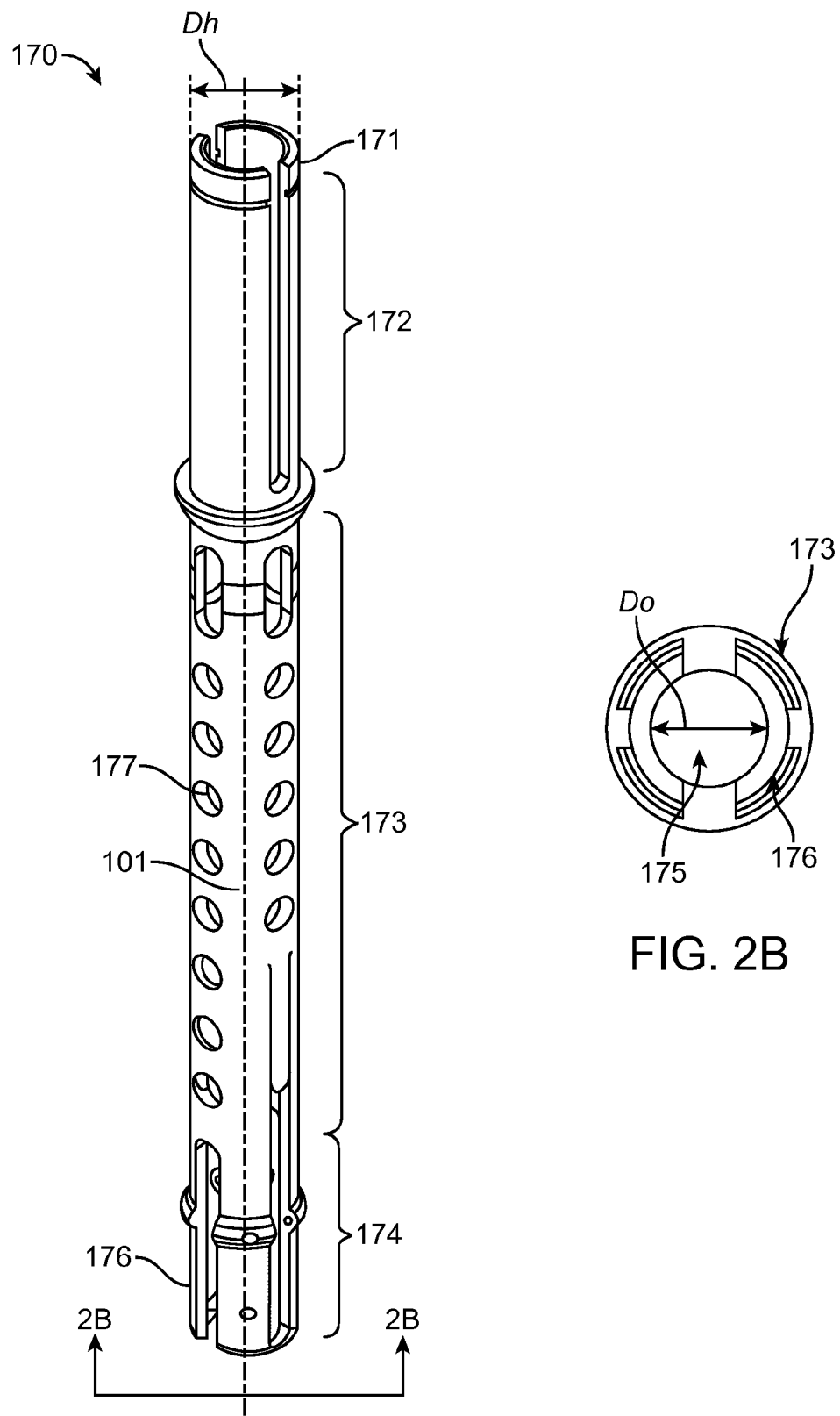

SPINAL INSTRUMENTS WITH SET SCREW LOADING AND RETENTION APPARATUS AND METHODS OF USE

CROSS-REFERENCE TO RELATED APPLICATIONS

This application claims priority to U.S. Provisional Patent Application No. 61/414,498, filed Nov. 17, 2010, which is incorporated herein by reference.

FIELD

The invention generally relates to methods and devices for the installation of spinal fixation systems, and more particularly to spinal instruments with a set screw loading and retention mechanism and methods of their use.

BACKGROUND

Spinal fixation systems typically require the threaded securement of some form of bone anchor and the like or bone screw-assembly into two or more vertebrae, as well as which requires the drawing of the rod to the anchors/screw-assemblies, or drawing the anchors/screw-assemblies to the rod. An exemplary bone screw-assembly 10, shown in FIG. 6, may be used with at least one other such assembly to secure a stabilization rod 19 and includes a pedicle screw 12 and a body member 14. The pedicle screw 12 may include a substantially spherical or elliptical head portion 24 defining a slot therein used to drive a threaded tube portion 28 into a vertebra. The body member 14 is generally cylindrical in configuration and adapted to receive the head portion 24 that cooperates therewith so as to define a modified ball-joint. This design allows for variable angular movement of the body member 14 with respect to the pedicle screw 12 with the threaded tube portion 28 extending through an opening 26 in the end of the body member 14. The body member 14 additionally defines a pair of opposed parallel slots (or a single slot) axially disposed in the side wall thereof forming a saddle to receive a portion of the fixation rod 19. A set screw 18, shown in FIG. 7, is used to threadably engage the body member 14 of the screw assembly 10 to secure the stabilizing rod 19 within the body member 14.

In various exemplary surgical procedures, one or more tubes may be coupled to the body member 14 prior to insertion of the set screw. The tubes may extend posteriorly away from the vertebra and may facilitate derotation and alignment of the spine, insertion of the rod, and insertion of set screws to rigidly fix the rod to the body member. For example, the tubes may include any of screw extender tubes, inner reduction tubes, outer sleeves of instruments, and outer reduction tubes in one or more configurations. A separate tool may be necessary to either draw the fixation rod down into the opposed slots in the body member of the screw assembly or, when necessary, to draw the pedicle screw and attached vertebrae outwardly to the rod to effect the desired alignment of the vertebrae and the securement of the rod. A screw driver may be used to insert the set screw through one or more of the tubes and to tighten the set screw after insertion of the rod.

Typically, the set screw is placed on the tip of the screw driver prior to insertion through one of the tubes at the surgical site. Typically, a friction fit may be employed between the set screw and the tip of the screw driver. Therefore, the set screws may fall off the screw driver onto the floor, into one of the tubes, or into the surgical site thus complicating the surgery with delays and possible contamination. The invention described herein may be used with any system that utilizes one or more tubes as described above to reduce the risk of any of these and other complications.

SUMMARY

Provided herein are systems, methods and apparatuses for a spinal instrument with a set screw loading and retention mechanism. A spinal instrument with a set screw loading and retention mechanism includes a first tube, a screw slot, and a retention mechanism. The first tube includes an inner lumen disposed concentric and proximate to a head portion of a bone screw. The screw slot is disposed along a portion of the first tube at a distance from the head portion of the bone screw and is configured for loading of a set screw for locking a spinal rod within the head portion of the bone screw. The retention mechanism is disposed along at least a portion of the inner tube configured to selectively retain the set screw. In other features, the first tube includes either an internal rod reduction tube or a screw extender tube.

In yet other features, a second tube is disposed generally concentric to and external to the first tube. The second tube includes either an external derotation/alignment tube or an external rod reduction tube. The second tube includes at least one slot for loading the set screw into the first tube and for viewing of the inner lumen, the set screw, and a screw driver that engages the set screw.

In still other features, the retention mechanism is distal to the screw slot. The retention mechanism is configured to temporarily engage the set screw to retain the set screw in the inner lumen and selectively disengage the set screw to release the set screw distally through the inner lumen. The retention mechanism includes a threaded portion including threading that mates with threading of the set screw to retain the set screw within the inner lumen. The retention mechanism includes a socket within the first tube and at least one of a pin, a ball, and a spring that retains the set screw within the inner lumen. The retention mechanism includes an angled surface of at least two angled facets protruding from the interior surface and into the inner tube lumen to retain with the screw.

An apparatus for loading and releasably retaining a set screw within a spinal instrument includes a first tube portion, a screw slot, and a retention mechanism. The first tube portion of the spinal instrument includes an outer surface and an inner surface defining an inner lumen. The screw slot is in communication with the outer surface and the inner surface of the tube portion and included dimensions for receiving the set screw. The retention mechanism is disposed proximate to the screw slot and releasably retains the set screw.

In other features, the instrument includes one of a screw extender and derotation/alignment instrument. A portion of the retention mechanism displaces relative to the inner lumen to release the set screw. The set screw rotates relative to the retention mechanism to be released. A second tube portion includes a slot in communication with the screw slot for receiving the set screw.

A method for loading and releasably retaining a set screw within a spinal instrument includes the step of providing a spinal instrument with a first tube including an inner lumen disposed concentric and proximate to a head portion of a bone screw, a screw slot disposed along a portion of the first tube at a distance from the head portion of the bone screw and configured for loading of a set screw for locking a spinal rod within the head portion of the bone screw, and a retention mechanism disposed along at least a portion of the inner tube configured to selectively retain the set screw. The method further includes the step of attaching the spinal instrument proximate to a bone screw assembly, loading a set screw through the screw slot such that the set screw is retained by the retention mechanism, and releasing the set screw from the retention mechanism to advance the set screw towards the bone screw assembly.

In other features, the method includes the steps of releasing the set screw from the retention mechanism includes rotating the set screw to disengage the retention mechanism, displacing at least one of a pin, a ball, and a spring of the retention mechanism to release the set screw, and performing one of an alignment procedure, a derotation procedure, a rod insertion procedure, and a rod reduction procedure after loading the set screw through the screw slot. The method includes the step of loading the set screw through a slot on a second tube disposed external to and concentric with the first tube.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several embodiments of the present invention.

FIG. 1A is a perspective view of an exemplary spinal instrument with a set screw loading and retention mechanism according to the principles of the present disclosure.

FIG. 1B is a view taken along 1B-1B of the distal end of the spinal instrument in FIG. 1A.

FIG. 2A is a perspective view of an exemplary outer tube of the spinal instrument according to the principles of the present disclosure.

FIG. 2B is a view taken along 2B-2B of the distal end of the outer tube in FIG. 2A.

DETAILED DESCRIPTION

Figure 3A:
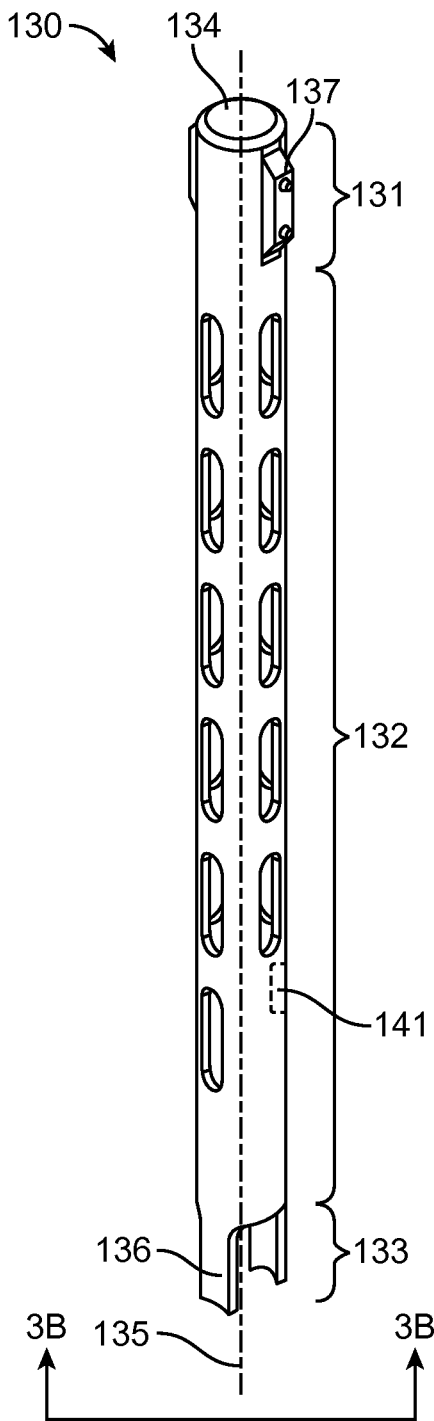
FIG. 3A is a perspective view of an exemplary inner tube of the spinal instrument according to the principles of the present disclosure.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

As shown in FIGS. 1A and 1B, a spinal instrument 100 includes a proximal portion 102 and a distal portion 104. The spinal instrument 100 includes a longitudinal axis 101, which is shown to be generally along the y-axis and along the proximal portion 102 to the distal portion 104. The spinal instrument 100 includes a transverse axis 103, which is shown to be generally along the x-axis. The spinal instrument 100 comprises an inner tube 130, an outer tube 170, an inner lumen 120, and a handle 110. The inner lumen 120 extends substantially along the longitudinal axis through the handle 110, the inner tube 130, and the outer tube 170.

In some examples, such as the examples of FIGS. 1-8B, the inner tube 130 may include an inner reduction tube for reducing a fixation rod 19 within a body member 14 of a screw assembly 10, and the outer tube 170 may attach to the body member 14 of the screw assembly 10. In other examples, such as the example of FIG. 9, the inner tube 130 may include a screw extender for attachment to the body member 14 of the screw assembly 10 that facilitates insertion of the fixation rod 19. The outer tube 170 may include an outer reduction tube that reduces the fixation rod 19 into the body member 14 of the screw assembly 10. An exemplary screw extender and reduction tube that may be used with the invention of the present disclosure may be found in commonly assigned U.S. Pub. No. 2010/0036443, entitled "Systems and Methods for Spinal Fixation" by Purcell et al. which is incorporated in its entirety herein by reference.

Figure 3B:
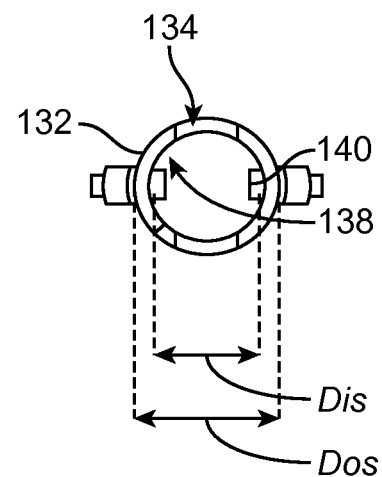
FIG. 3B is a view taken along 3B-3B of the distal end of the inner tube in FIG. 3A.

In the present example, the inner tube 130 of FIGS. 3A and 3B is configured as an inner reduction tube coaxially positioned within the outer tube 170 of FIGS. 2A and 2B. The inner tube 130 and the outer tube 170 are removably and operably coupled to the handle 110. The inner tube 130 includes a retention mechanism 140 placed along the interior surface 138 (as shown in FIG. 3B) of the inner tube 130 and a screw slot 141 disposed along at least a portion of the inner tube 130 (as shown in FIG. 3A), which allows for the insertion of a set screw, such as set screw 18 shown in FIG. 6, through the screw slot 141 and the accommodation of the set screw 18 to be preloaded within the inner tube 130 at a particular longitudinal position. The screw slot 141 accommodates and permits the set screw 18 to pass through the exterior surface of the inner tube 130 to engage the retention mechanism 140. The retention mechanism 140 holds the set screw 18 and allows the surgeon or operator of the spinal instrument 100 to tighten the set screw 18 after a pedicle screw has been set for spinal deformity surgery. The retention mechanism 140 then releases the set screw 18 for the tightening of the set screw 18. Any type of set screw 18 may be used that includes a length L, which may be accommodated by the screw slot 141. The surgeon may perform derotation, alignment, rod insertion, rod reduction, and/or other procedures with the set screw 18 retain within the inner tube 130.

Figure 6:
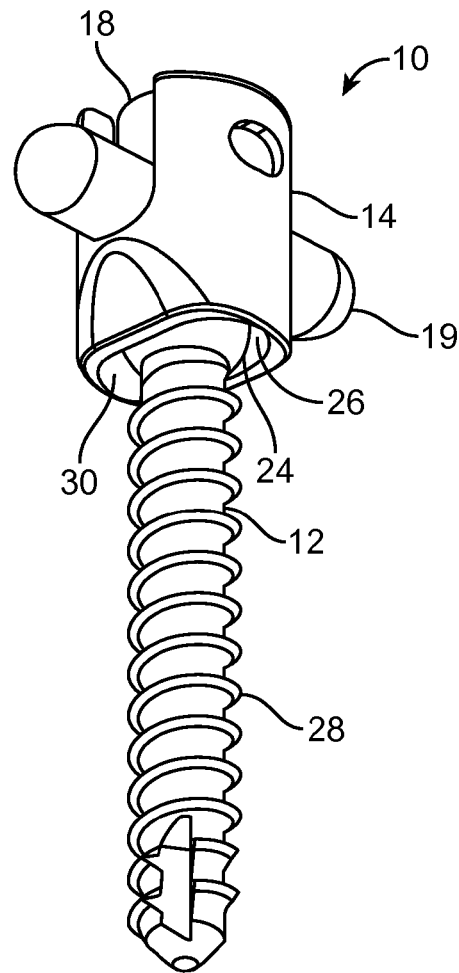
FIG. 6 is a perspective view of an exemplary pedicle screw assembly according to the principles of the present disclosure.

An example of an assembled spinal screw assembly 10 is seen in FIG. 6. The spinal screw assembly 10 comprises the pedicle screw 12, the body member 14, bushing (not shown), and the set screw 18. The assembly 10 is used with at least one other such assembly and a stabilization or fixation rod 19 to connect the assemblies and stabilize the vertebrae into which the assemblies are inserted. The pedicle screw 12 preferably employed in assembly 10 has a spherical head defining a slot therein used to drive the screw into the bone. The rounded surface 24 defined by the lower portion of screw head rests upon and mates with a rounded interior surface 26 formed in the inner or lower end of the body member 14 of the assembly 10 so as to form a modified ball joint that provides the desired variable angular movement of the body member with respect to the embedded pedicle screw. The threaded tube portion 28 of screw 12 extends therefrom through the opening 30 in the lower end of body member 14.

Figure 7:
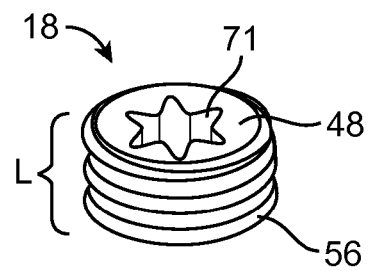
FIG. 7 is a perspective view of an exemplary set screw according to the principles of the present disclosure.

To secure the fixation rod 19 within the body member 14 of the assembly, the set screw 18 is provided, as shown in FIG. 7. The set screw 18 defines a top portion 48 and a plurality of axially aligned threads 56 adopted to engage threads (not shown) on the opposed interior side walls of the body member 14, as known in the art. The set screw 18 includes a length L, which is to be accommodated by the screw slot 141. As such, the screw slot 141 can be adjusted to the length L of a set screw to allow the set screw to pass through the exterior surface of the inner tube 130 to the inner tube lumen 134 therein.

Upon securing the bushing in the body member 14 and the fixation rod 19 in a seat of the bushing, the set screw 18 is axially aligned with the body member 14. Upon pressing the set screw 18 downwardly into body member 14, the threads on the interior of the body 14 and threads 56 interlock so as to allow the set screw 18 to be tightened downwardly. As set screw 18 is tightened into the body member 14 of the assembly 10, the planar bottom surface of the set screw 18 abuts the fixation rod 19 and presses the rod 19 into and against a seat formed on the upper end of bushing. The resulting pressure on the bushing causes the tapered surfaces on the lower end of the bushing to press against the rounded surface of the screw head, thereby securing the rod 19 in seat and providing decentralized and evenly distributed force acting along the longitudinal axis of the screw 12. Thus, the use of the bushing creates a taper lock between the pedicle screw and body member and increases the area of contact therebetween. The result is an improved retention securement over that provided by the earlier described direct contact of the fixation rod against the upper end of the screw head.

FIG. 7 illustrates the set screw 18 having a generally cylindrical perimeter portion in which the threads 56 project radially. The threads 56 may engage the retention mechanism 140. The set screw 18 includes a length L, which is to be accommodated by the screw slot 141 in order to pass through the exterior surface of the inner tube 130. The set screw 18 is for a polyaxial screw; however, any type of set screw may be used that includes a length L, which may be accommodated by the screw slot 141 to pass through the exterior surface of the inner tube 130. The set screw 18 will allow the surgeon to tighten the clamping force on the fixation rod 19 by simply pressing downwardly on and/or rotating the set screw 18. A hexagonally configured slot 71 is provided in the top portion 48 of set screw 18 to facilitate the rotation of the set screw with a suitably sized mating tool.

As shown in FIGS. 2A-B, the outer tube 170 includes a proximal portion 171, a handle portion 172, a tube portion 173, and a distal portion 174. The outer tube 170 includes an outer tube lumen 175 that extends substantially along the longitudinal axis 101 through the proximal portion 171, the handle portion 172, the distal portion 173, and the tube portion 174. The tube portion 173 includes a plurality of slots 177 that communicate with the exterior of the tube portion 173 and the outer tube lumen 175. While the embodiment shown in FIGS. 2A-B employs many slots, the invention includes any embodiment with at least one slot 177. The slot 177 may align with the screw slot 141 to facilitate insertion of the set screw 18. The outer tube lumen 175 includes a diameter Do, and the handle portion includes a diameter Dh. The distal portion 174 may include a plurality of prongs 176, which may be used to attach to the body member 14 of the screw assembly 10.

As shown in FIGS. 3A-B, the inner tube 130 includes a proximal portion 131, an inner tube portion 132, and a distal portion 133. The inner tube 130 includes a central longitudinal axis 135 and generally a circular cross-sectional profile. Alternatively, the inner tube 130 may include alternative cross-section profiles, such as elliptical, square, polygonal, trapezoidal, hexagonal, and the like. The inner tube 130 includes an inner tube lumen 134 that extends substantially along the longitudinal axis 135 through the proximal portion 131, the tube portion 132, and the distal portion 133. The inner tube 130 includes the interior surface 138, which borders the inner tube lumen 134. The screw slot 141 may be positioned along at least a portion of the longitudinal length of the inner tube 130 to allow the set screw 18 to pass through the interior surface 138 into the inner tube lumen 134 and engage the retention mechanism 140. The retention mechanism 140 is sized and positioned to accommodate a set screw positioned along at least a portion of the inner lumen 134 and the interior surface 138.

The retention mechanism 140 may be positioned along at least a portion of the longitudinal length of the interior surface 138, such that the set screw 18 may be locked at a particular longitudinal position in the inner tube 130. The retention mechanism 140 may be a variety of geometric retention mechanisms that can temporarily lock or engage the set screw 18 in the inner lumen 134 along at least a portion of the inner lumen 134, which can then be disengaged to permit the set screw 18 to pass through the retention mechanism 140 along the longitudinal axis 138 and towards the distal portion 133 of the inner tube 130. One or more viewing windows 143 may be disposed along the inner tube 130. In some examples, one or more of the windows 143 may be adjacent and proximate to the screw slot 141. The viewing windows 143 and slots 177 of the outer tube 170 may align to enable clear view to the inner lumen 134 and thus enable the surgeon to view interaction of the set screw 18 and associated instruments such as a screw driver.

The distal portion 133 of the inner tube 130 may include a plurality of tongs 136, which are sized to approximate and hold the spinal rod into the screw head. The proximal portion 131 may include a plurality of tabs 137, which may operably connect with the slots or openings 177 of the outer tube 170. While two tabs 137 are employed in the embodiment shown in FIGS. 3A-B, the invention may include any number of tabs or no tabs as shown as FIG. 9. The inner tube 130 includes an outer diameter Dos and an inner diameter Dis that approximates the interior surface 138. In one embodiment, the diameter Dos is smaller than the diameter Do of the outer tube lumen 175, such that the inner tube portion 132 is rotatable within the outer tube lumen 175. In one embodiment, the diameter Dis is formed to fit the circumference of the set screw 18 and allow the set screw 18 to pass through the diameter Dis of the inner tube lumen 134. The inner tube lumen 134 may also be formed as to allow a screwdriver to be passed through the inner tube lumen 134.

Figure 4A:
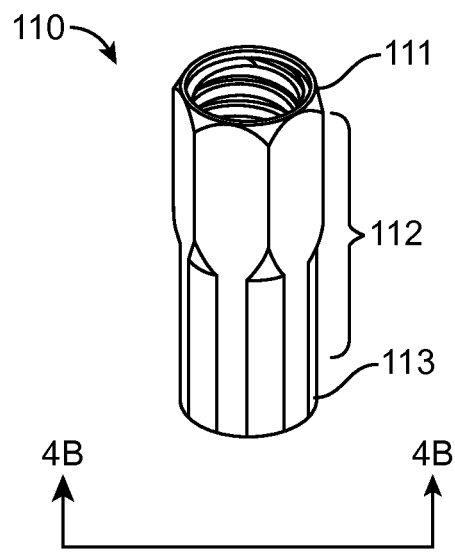
FIG. 4A is a perspective view of an exemplary handle according to the principles of the present disclosure.
Figure 4B:
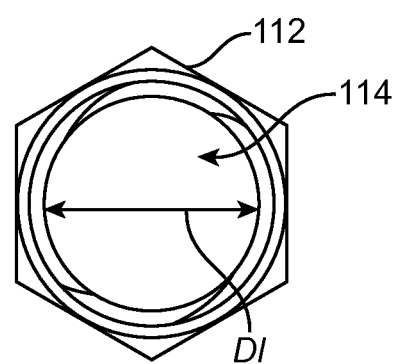
FIG. 4B is a view taken along 4B-4B of the distal end of the handle in FIG. 4A.

As shown in FIGS. 4A-B, the handle 110 may include a proximal portion 111, a handle tube portion 112, and a distal portion 113. The handle 110 includes a handle lumen 114 that extends substantially along the longitudinal axis through the proximal portion 111 and the distal portion 113. The handle lumen 114 includes a diameter of Dl, whereby the diameter Dl is greater than the diameter Dh of the handle portion 172, such that the handle lumen 114 is operably engaged with the handle portion 172 of the outer tube 170. The handle 110 may operably position or maneuver the inner tube 130 and/or the outer tube 170. Generally, the handle 110 includes a hexagonal cross-sectional profile, as shown in FIG. 4B, alternative cross-sectional profiles, such as square, rectangular, polygonal, elliptical, trapezoidal, pentagonal, or octagonal may be selected for the cross-sectional profile of the handle 110.

In the present example, the retention mechanism 140 is positioned distally from the screw slot 141, as shown in FIGS. 5A-5E, such that when the set screw 18 passes through the screw slot 141, the set screw 18 will move distally to engage the retention mechanism 140. Alternatively, the retention mechanism 140 may be positioned proximally from the screw slot 141 to prevent migration of the set screw 18 proximally from the screw slot 141. For example, two retention mechanisms 140 may be used to retain the set screw 18 *a* prevent migrating both distally and proximally from the screw slot 141. The inner tube 130 includes the screw slot 141 located along at least a portion of the inner tube lumen 134 and the retention mechanism 140 located at a distal portion relative to the screw slot 141. Preferably the size of the screw slot 141 accommodates the length of the set screw 18 to be used, which is further described below with reference to FIG. 7.

Figure 5A:
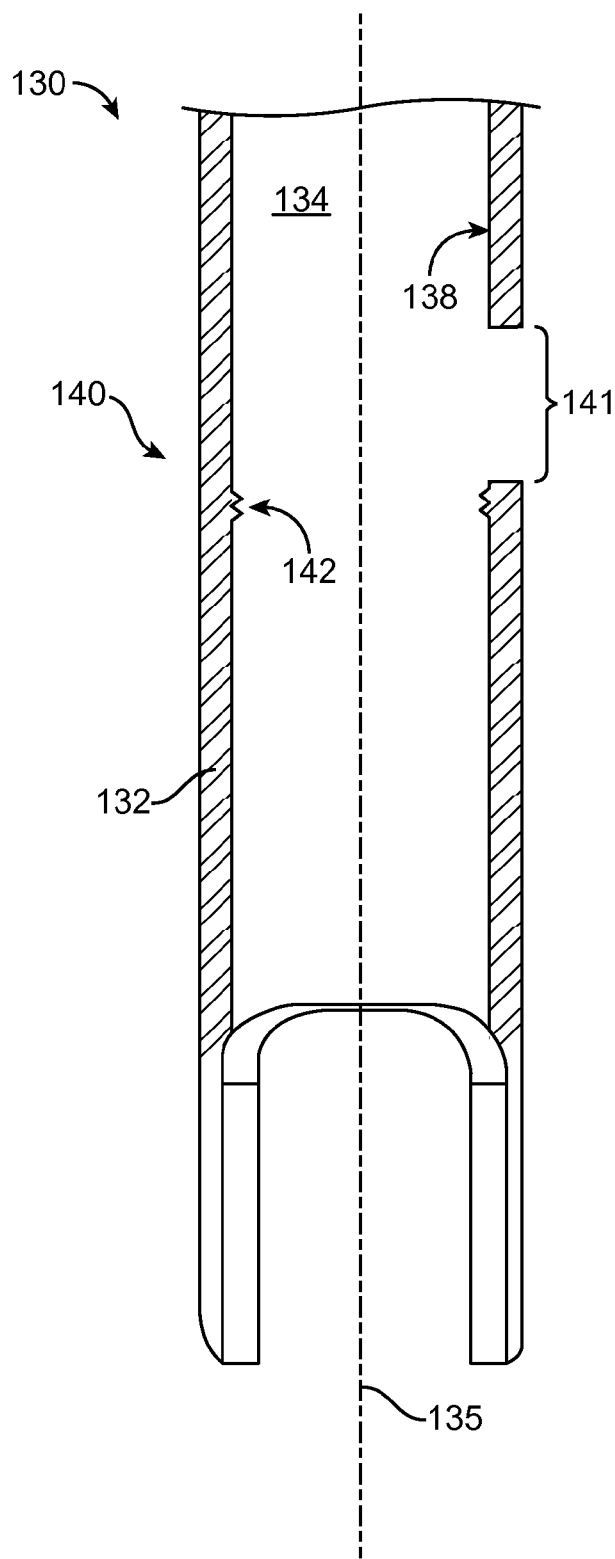
FIG. 5A-5E are partial cross-sectional views of the inner tube showing various exemplary loading and retention mechanisms according to the principles of the present disclosure.

In one embodiment shown in FIG. 5A, the retention mechanism 140 includes a threaded portion 142 on at least a portion of the inner tube lumen 134, where the set screw 18 engages the threaded portion 142 after passing through the screw slot 141. Alternatively, the threaded portion 142 is located substantially about the interior surface 138 of the inner tube lumen 134 along at least a portion of the longitudinal axis 135 of the inner tube 130. In one embodiment, the threaded portion 142 is disposed about the circumference of the interior surface 138; alternatively, the threaded portion 142 may be disposed about at least a portion of the circumference of the interior surface 138. The threaded portion 142 may be formed to accept the set screw 18 with the threaded portion 56 on the outer perimeter of the set screw 18. The threaded portion 142 may include quarter-turn thread, a full-turn thread, a ¾-turn thread, a ½-turn thread, or thread between about a one-full turn thread and about one quarter-turn thread.

Figure 5B:
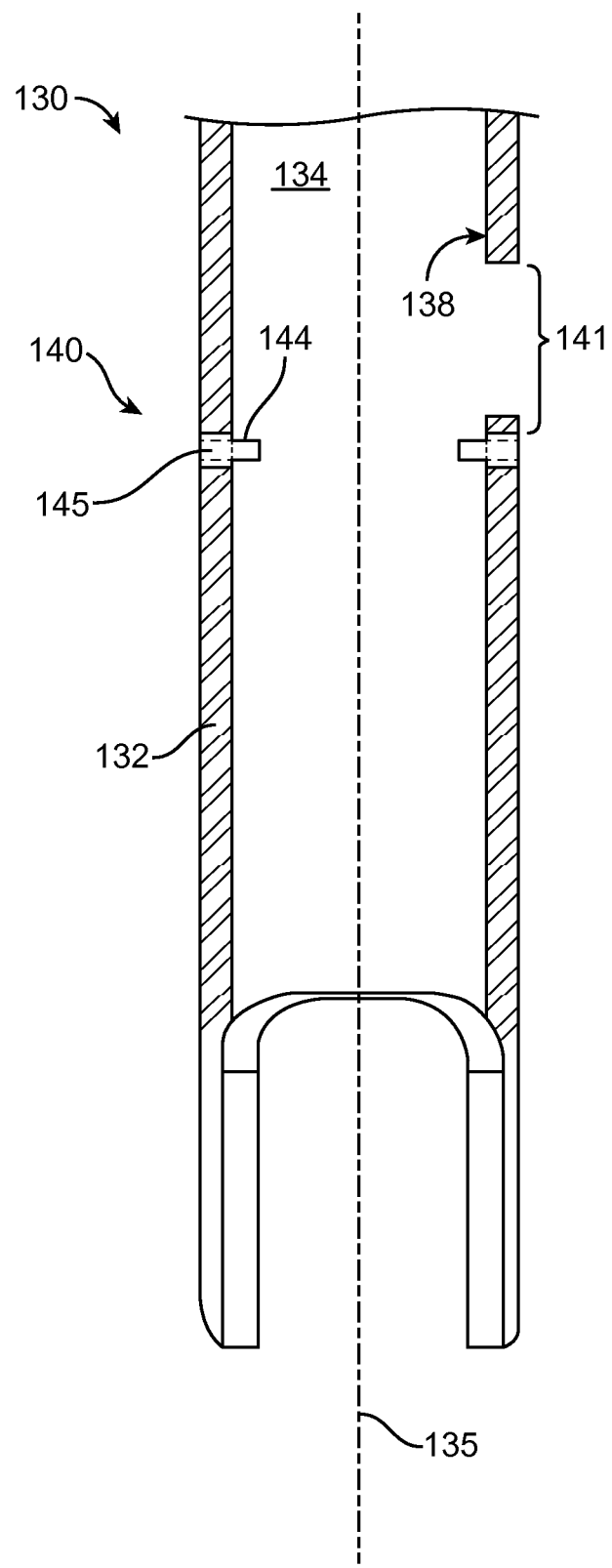

As shown in FIG. 5B, another embodiment of the retention mechanism 140 includes a pin 144. The pin 144 is located along at least a portion of the inner tube lumen 134 and positioned distally from the screw slot 141. The pin 144 protrudes from the interior surface 138 and is able to deform or displace towards the tube portion 132 into a pin lumen 145 and away from the central longitudinal axis 135 of the inner tube 130. Alternatively, the pin 144 may remain static in position relative to the longitudinal axis 135. In one embodiment, the pin 144 is rectangular in shape; alternatively, the pin 144 may be square, polygonal, trapezoidal, pentagonal, hexagonal, cylindrical, and the like configurations. Alternatively, the pin 144 may be a circular pin that is disposed about the circumference of the inner tube lumen 134 along at least a portion of the inner tube 130. In one embodiment, the retention mechanism 140 may be an O-ring. Preferably, the pin 144 is shaped and sized as to retain the set screw 18; alternatively, the pin 144 may engage with the threaded portion 56 of the set screw 18.

Figure 5C:
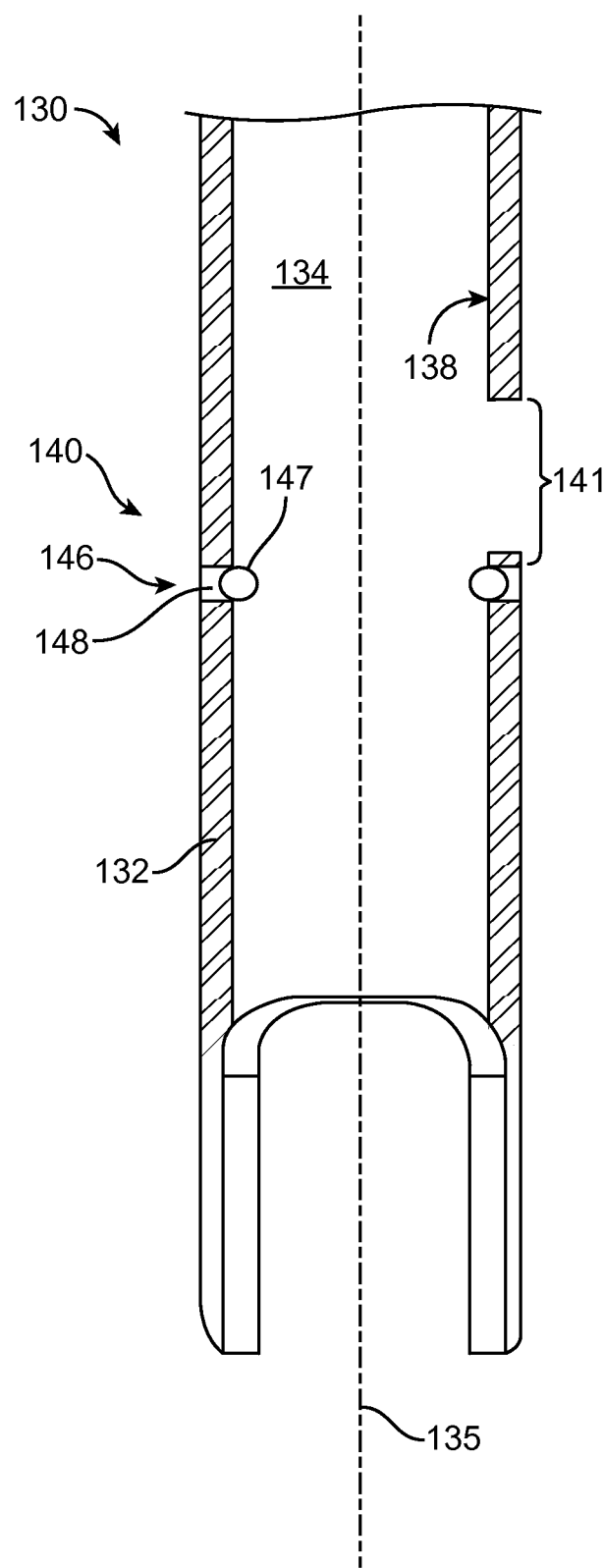

As shown in FIG. 5C, another embodiment of the retention mechanism 140 is a ball joint lock 146 that is positioned distally from the screw slot 141. The ball joint lock 146 includes a ball 147 protruding from at least a portion from the interior surface 138 and a socket 148 disposed in at least a portion of the inner tube 132, in which the ball 147 is held in the socket 148 and retains the set screw 18 in the inner tube lumen 134 at a position within the inner tube lumen 134. The ball 147 is displaced in the socket 148 when the set screw 18 is advanced towards the distal portion 133 of the inner tube 130, which then allows the set screw 18 to be advanced by an operator. In one embodiment, the ball 147 includes a generally spherical configuration. Alternatively, the ball 147 may include a curved or ellipsoidal configuration.

Figure 5D:
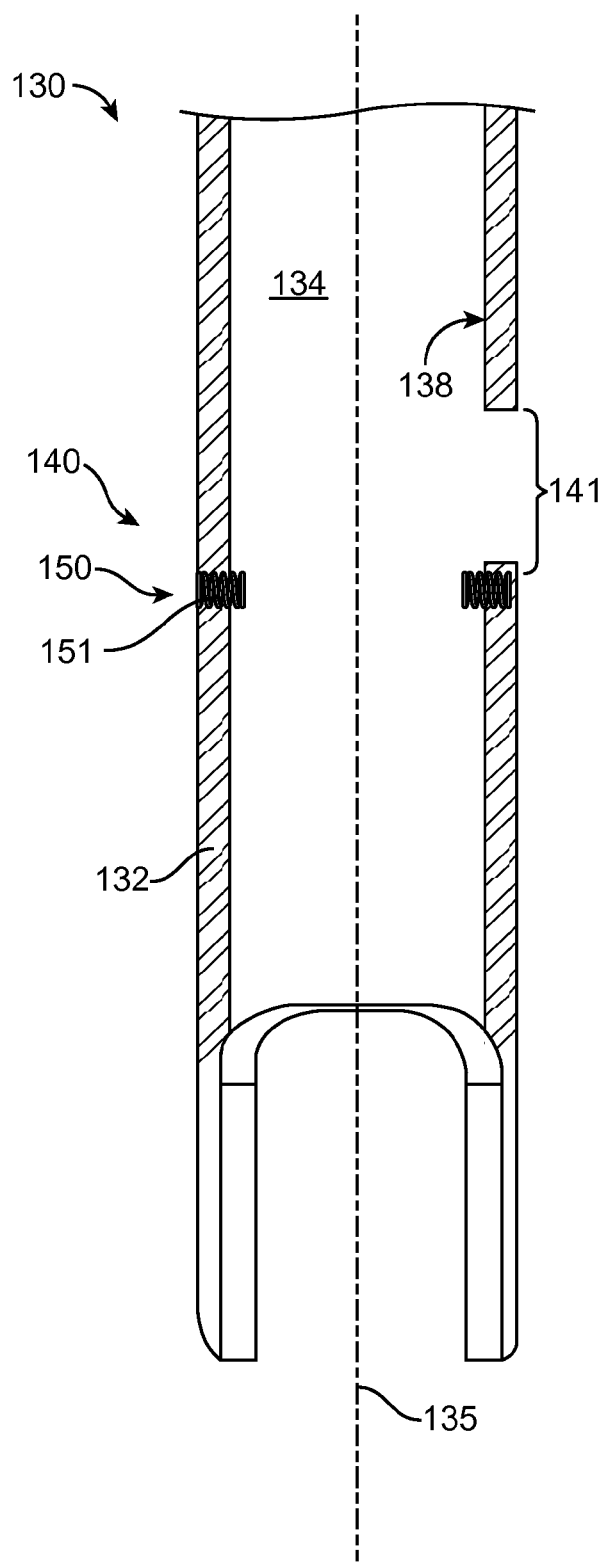

As shown in FIG. 5D, another embodiment of the retention mechanism 140 is a spring lock 150 that is positioned distally from the screw slot 141. The spring lock 150 includes a spring 151 located along at least a portion of the inner tube 132 and protruding from the interior surface 138 and towards the central longitudinal axis 135 within the inner tube lumen 134. The spring 151 retains the screw 18 at a particular longitudinal position of the inner tube lumen 134 and when the set screw 18 is advanced along the longitudinal axis 135 towards the distal portion 133 of the inner tube 130, the spring 151 compresses axially away from the longitudinal axis 135 and towards the tube portion 132 to permit the set screw 18 to advance towards the distal portion 133 and pass through the retention mechanism 140. In one embodiment, at least two springs 151 are located along the inner tube portion 132; alternatively, more than two springs 151 may be disposed along the circumference of the inner tube portion 132. For example, three springs may be disposed at equidistant lengths from each other along the inner tube portion 132. The greater number of springs 151 disposed about the inner tube lumen 134 provides increased contact between the retention mechanism 140 and the set screw 18. Although spring 151 in FIG. 5D is a coil spring extending substantially perpendicular to the longitudinal axis 135, other springs, such as a leaf spring, may likewise retain the set screw 18. For example, a leaf spring may attach to the interior surface 138 and include a distal end extending from the interior surface 138 towards the longitudinal axis 135.

Figure 5E:
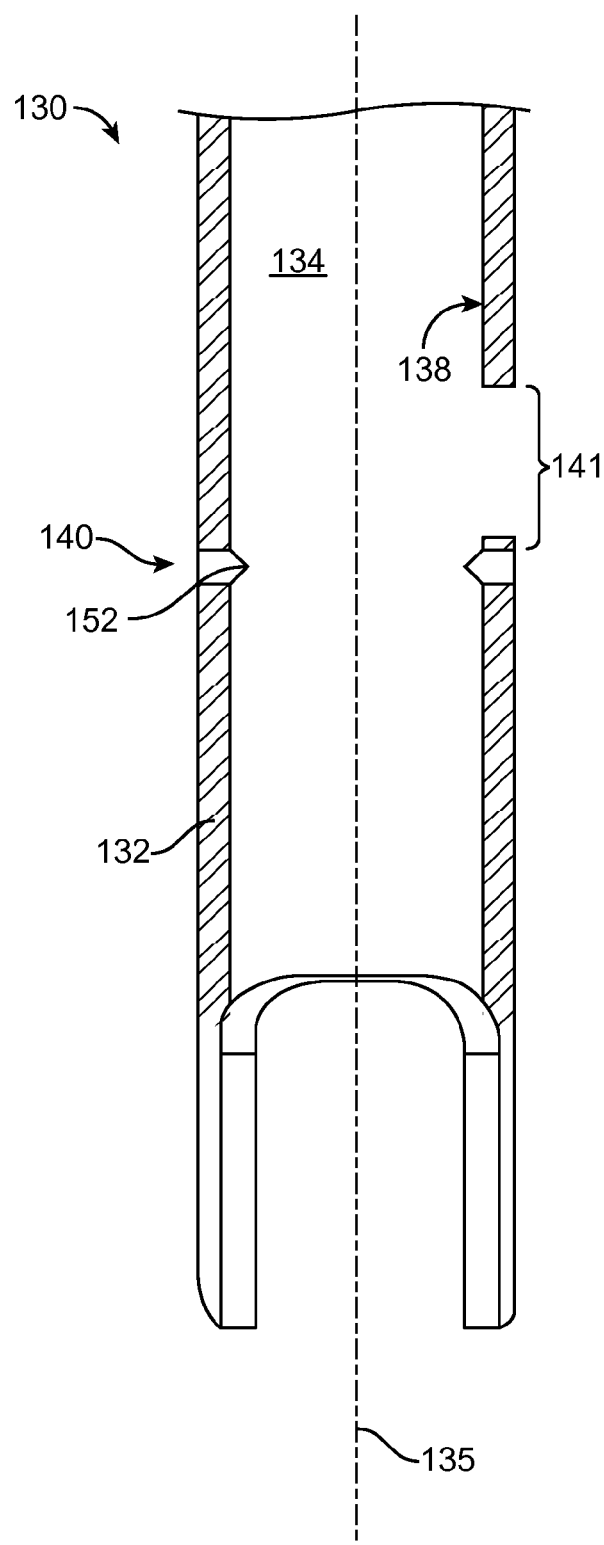

As shown in FIG. 5E, another embodiment of the retention mechanism 140 is an angled surface 152 that is positioned distally from the screw slot 141. The angled surface 152 includes at least two angled facets protruding from the interior surface 138 and into the inner tube lumen 134 to retain the set screw 18. In one embodiment, the angled surface 152 includes a triangular facet; alternatively, the angled surface 152 may include square, rectangular, polygonal, trapezoidal, elliptical, hexagonal facets to permit the set screw 18 to be retained therein. The angled surface 152 may comprise a polymer-like material to slip-fit the set screw 18 within the screw slot 141 and lumen 134.

Figure 8A:
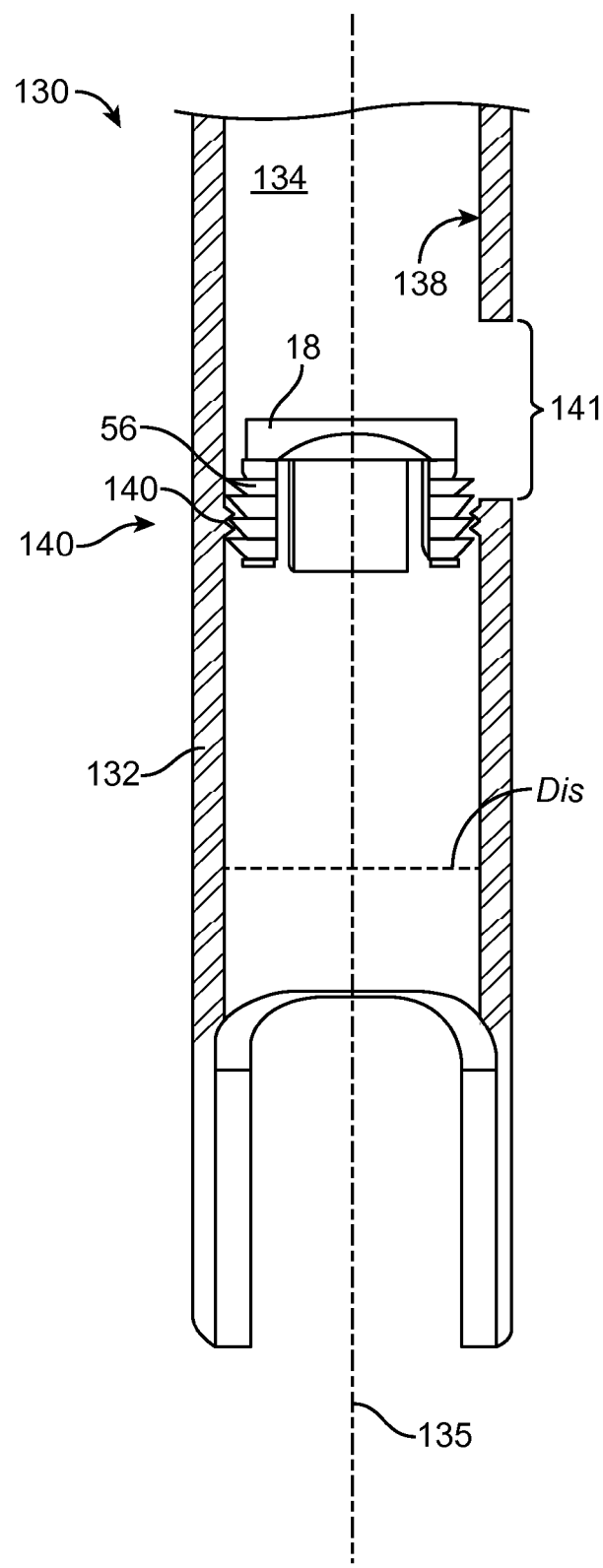
FIGS. 8A and 8B are partial cross-sectional views of various exemplary set screws retained within the inner tube of the spinal instrument according to the principles of the present disclosure.
Figure 8B:
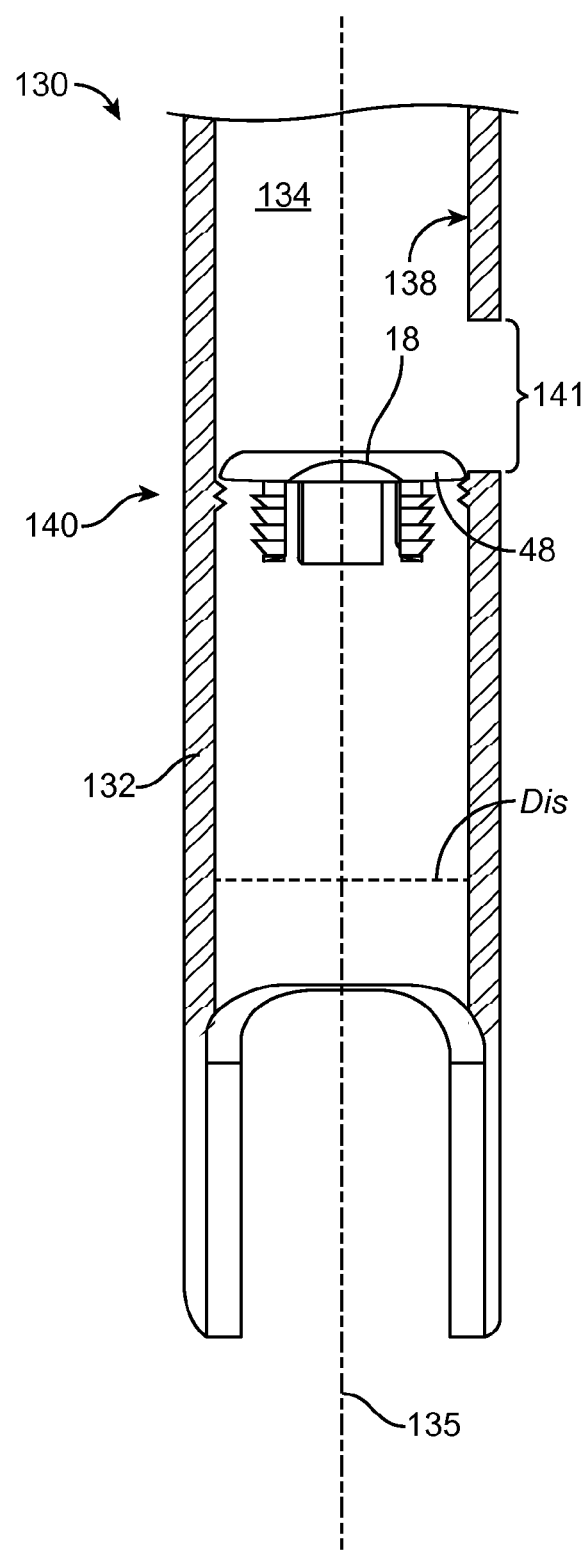
Figure 9:
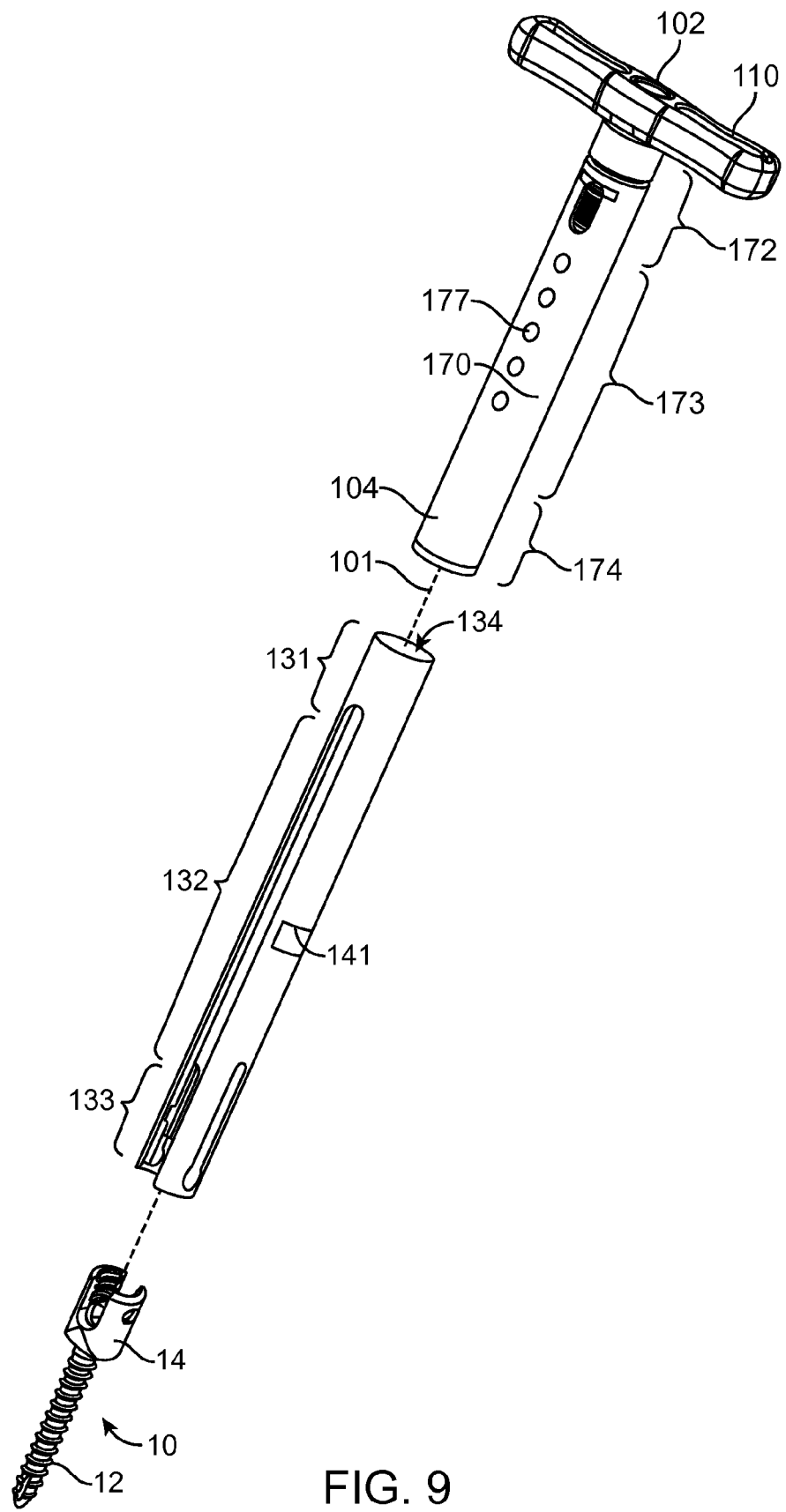
FIG. 9 is a perspective view of another exemplary spinal instrument including an inner tube screw extender and an outer tube rod reducer with a set screw loading and retention mechanism according to the principles of the present disclosure.

FIGS. 8A-8B illustrates the set screw 18 retained with one embodiment of the retention mechanism 140 in the inner tube portion 132. As shown in FIG. 8A, in one embodiment, the set screw 18 passes through the screw slot 141 into the inner tube lumen 134 to engage the retention mechanism 140. The threads 56 of the set screw 18 have a generally cylindrical perimeter portion in which the threads 56 project radially therefrom. Alternatively, the threads 56 may be a plurality of threads. The inner diameter Dis of the inner tube portion 132 approximates the set screw 18, as to allow the set screw 18 to pass through the inner tube lumen 134 but allows for the retention mechanism to selectively engage and disengage the set screw 18 along the threads 56.

As shown in FIG. 8B, the top portion 48 of set screw 18 is engaged with the retention mechanism 140, such that the top portion 48 engages with the retention mechanism 140 at a fixed position along the longitudinal axis 135 of the inner tube 130. The inner diameter Dis of the inner tube portion 132 approximates the set screw 18, as to allow the set screw 18 to pass through the inner tube lumen 134 but allows for the retention mechanism 140 to selectively engage and disengage the top portion 48 of the set screw 18.

Referring again to FIG. 2A, in the present example, one or more of the slots 177 of the outer tube 170 may also be configured similar to the screw slot 141 of the inner tube 130 to allow for insertion of the set screw 18 into the inner lumen 134. This allows the set screw 18 to be preloaded within the inner tube 130 at a particular longitudinal position while the outer tube 170 remains secured over the inner tube 130. For example, the inner tube 130 may be retained within the outer tube 170 when the outer tube 170 attaches to the body member 14 for use during a derotation and alignment procedure. The outer tube 170 may be rotated until one of the slots 177 aligns with the screw slot 141. The set screw 18 may then be inserted into the inner lumen 134 where the retention mechanism 140 retains the set screw 18 therein. The slots 177 may also provide viewing windows to allow a surgeon to view and confirm engagement between an instrument, such as a screwdriver, with the set screw 18.

Referring back to FIG. 9, in other examples in which the inner tube 130 functions as a screw extender and the outer tube 170 functions as an outer reduction tube, the single screw slot 141 may suffice for insertion of the set screw 18 into the inner lumen 134. For example, the distal portion 133 of the inner tube 130 may be attached to the body member 14 to facilitate insertion of the rod 19 of FIG. 6 during an MIS fusion procedure. The set screw 18 may then be inserted into the inner lumen 134 where the retention mechanism 140 retains the set screw 18 therein. The outer tube 170 may then slide over the inner tube 130 to reduce the fixation rod 19 into the body member 14 during a rod reduction procedure.

Generally, the method for retention a set screw in the spinal instrument includes providing a retention mechanism along the interior surface of an inner tube; accommodating a set screw into the retention mechanism to lock the set screw along the longitudinal axis of the inner tube; and disengaging the set screw from the retention mechanism to tighten the set screw in a pedicle screw assembly.

As can be understood by one skilled in the art, the spinal instrument 100 and the retention mechanism 140 and/or any of its components may have any size, shape, length, thickness, height, weight, or any other parameters. Such parameters may be selected by the surgeon (or other qualified professional) for performance of specific procedures. Further, the spinal instrument 100 and the retention mechanism 140 and/or any of its components may be manufactured from metal, plastic, synthetic material, or other suitable materials, or any combination thereof. Preferably, the spinal instrument 100 and the retention mechanism 140 are formed from titanium or stainless steel or other alloys. Alternatively, the spinal instrument 100 and the retention mechanism 140 are formed from Polyether ether ketone (PEEK), which is a colorless organic polymer thermoplastic.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. A spinal instrument with a set screw loading and retention mechanism comprising:
   a first tube including an inner lumen disposed concentric and proximate to a head portion of a bone screw;
   a screw slot disposed along a portion of the first tube at a distance from the head portion of the bone screw and configured for loading of a set screw for locking a spinal rod within the head portion of the bone screw; and
   a retention mechanism disposed along an interior surface of at least a portion of the inner tube distal to the screw slot that is configured to selectively retain the set screw, wherein the retention mechanism includes a threaded portion including threading that mates with threading of the set screw to retain the set screw within the inner lumen adjacent and proximate to the screw slot.

2. The spinal instrument of claim 1, further comprising a second tube disposed generally concentric to and external to the first tube.

3. The spinal instrument of claim 2, wherein the second tube comprises one of an external derotation/alignment tube and an external rod reduction tube.

4. The spinal instrument of claim 2, wherein the second tube includes at least one slot for loading the set screw into the first tube and for viewing of the inner lumen, the set screw, and a screw driver that engages the set screw.

5. The spinal instrument of claim 1, wherein the retention mechanism is configured to temporarily engage the set screw to retain the set screw in the inner lumen and selectively disengage the set screw to release the set screw distally through the inner lumen.

6. The spinal instrument of claim 1, wherein the first tube comprises an internal rod reduction tube.

* * * * *